United States Patent
Sluijter et al.

[11] Patent Number: 6,161,048
[45] Date of Patent: *Dec. 12, 2000

[54] METHOD AND SYSTEM FOR NEURAL TISSUE MODIFICATION

[75] Inventors: Menno E. Sluijter, Amsterdam, Netherlands; William J. Rittman, III, Lynnfield; Eric R. Cosman, Belmont, both of Mass.

[73] Assignee: Radionics, Inc., Burlington, Mass.

[*] Notice: This patent is subject to a terminal disclaimer.

[21] Appl. No.: 09/297,316

[22] PCT Filed: Jun. 26, 1997

[86] PCT No.: PCT/US97/11145

§ 371 Date: Sep. 22, 1999

§ 102(e) Date: Sep. 22, 1999

[87] PCT Pub. No.: WO97/49453

PCT Pub. Date: Dec. 31, 1997

[51] Int. Cl.$^7$ .................................................. A61F 2/00
[52] U.S. Cl. ............................................................ 607/100
[58] Field of Search ........................ 607/89, 99–102, 607/113, 148; 606/34, 41; 600/547, 549, 373

[56] References Cited

U.S. PATENT DOCUMENTS

| | | | |
|---|---|---|---|
| 4,907,589 | 3/1990 | Cosman | 607/113 X |
| 5,233,515 | 8/1993 | Cosman | 600/301 X |
| 5,433,739 | 7/1995 | Sluijter et al. | 607/113 X |
| 5,951,546 | 9/1999 | Lorentzen | 606/41 |
| 5,983,141 | 11/1999 | Sluijter et al. | 607/100 |

FOREIGN PATENT DOCUMENTS

| | | |
|---|---|---|
| 85/01213 | 3/1985 | WIPO . |
| 94/00188 | 1/1994 | WIPO . |
| 97/13550 | 4/1997 | WIPO . |

OTHER PUBLICATIONS

Cosman, et al.; Theoretical Aspects of Radiofrequency Lesions and the Dorsal Root Entry Zone; (1984); Neurosurgery; 15: pp. 945–950.

Cosman, et al,; Method of Making Nervous System Lesions, in Wilkins RH, Rengachary SS (eds); (1984); Neurosurgery, vol. III; pp. 2490–2498.

Salkoff; Temperature–induced seizure and frequency–dependent neuromuscular block in a ts mutant drosophilia; (1978); Nature (UK); 273, No. 5658: pp. 156–158.

Guttman, et al.; Squid axon membrane response to white noise stimulation; (1974); Biophys. J. (USA); 14, No. 12: pp. 941–955.

*Primary Examiner*—Cary O'Connor
*Assistant Examiner*—Ryan Carter

[57] ABSTRACT

A method and apparatus for altering a function of neural tissue in a patient. An electromagnetic signal is applied to the neural tissue through an electrode. The electromagnetic signal has a frequency component above the physiological stimulation frequency range and an intensity sufficient to produce an alteration of the neural tissue, the alteration causing the patient to experience a reduction in pain, and a waveform that prevents lethal temperature elevation of the neural tissue during application of the electromagnetic signal to the neural tissue.

9 Claims, 7 Drawing Sheets

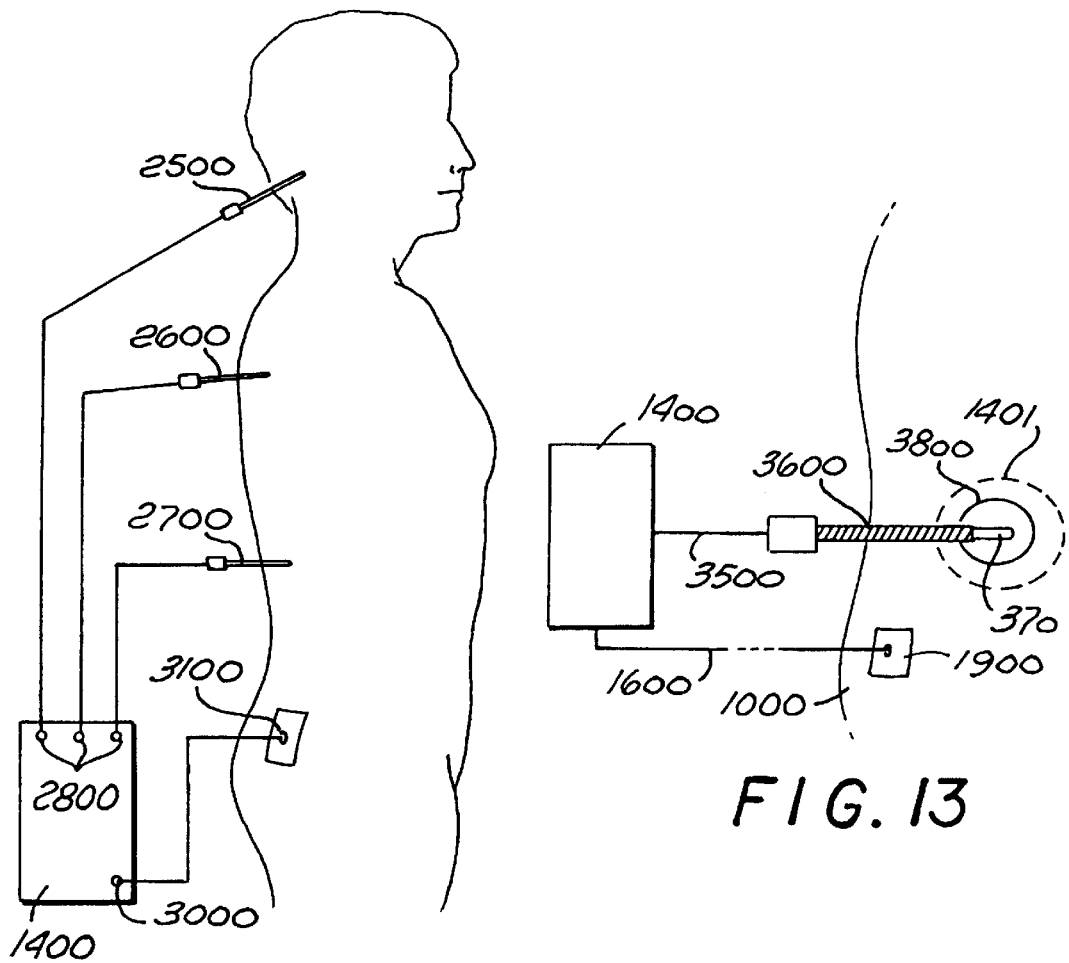
FIG. 12
FIG. 13
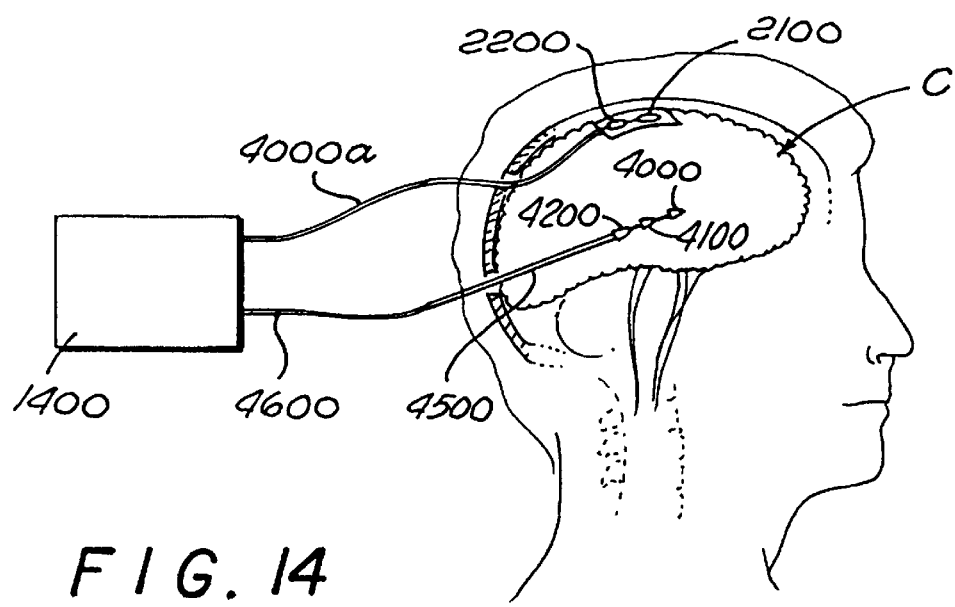
FIG. 14

METHOD AND SYSTEM FOR NEURAL TISSUE MODIFICATION

FIELD OF THE INVENTION

This invention relates generally to technological advances in the medical field and systems and procedures for prolonging and improving human life. More particularly, this invention relates to a method and system for altering or modifying neural tissue in a human body by using a modulated radiofrequency generator coupled to a signal applicator system that is strategically located in tissue near a patient's neural system to relieve pain without heating it to lethal levels.

BACKGROUND OF THE INVENTION

In the past, radiofrequency (RF) generators and electrodes have been applied near or in neural tissue, for relieving pain or modifying its function. By way of one example, a lesion generator identified by Model No. RFG-3C RF, available from a company named Radionics, Inc., located in Burlington, Mass., has electrodes, which may be placed near a desired neural tissue area. The desired neural tissue area is heated by radiofrequency (RF) resistive power dissipation of the generator power deposited in the tissue. In some cases, thermal monitoring by a thermo sensor in the electrode is used to control the process. It is common to form heat lesions with tissue temperatures ranging from 60 to 95 degrees Celcius (° C.). Tissue generally dies when heated to about 45° C. to 50° C., which causes the patient to suffer severe, if not, unbearable pain. The pain levels are so intense, that local or general anesthetic is often required during such a procedure. Use of local or general anesthetic exposes a patient to undesired risks, and the destructive nature of and unpleasant side effects of the radiofrequency (RF) heat lesions are limitations of this technique, which is well known. Heat lesion generators typically use continuous wave radiofrequency (RF) generators with radiofrequency ranges from 100 Kilo Hertz to several Mega Hertz. Heat lesion generators are available from several companies such as Radionics, Fisher, OWL, Elekta, Medtronic, Osypka, EPT, and so on. The theoretical aspects and use of RF lesion generators and electrodes for relieving pain and functional disorders is discussed in various papers, two of which are: (1) Cosman, et al., "Theoretical Aspects of Radiofrequency Lesions and the Dorsal Root Entry Zone," *Neurosurgery* 15:945–950, 1984; and (2) Cosman E R and Cosman B J, "Methods of Making Nervous System Lesions," in Wilkins R H, Rengachary SS (eds): *Neurosurgery,* New York, McGraw-Hill, Vol. III, 2490–2498, 1984.

Neural stimulation has also recently become a common method for pain therapy. For neural stimulation, stimulus generators are generally used, which typically have output levels between 0 to 10 volts (or zero to several milliamperes of current criteria are used). A variety of waveforms and pulse trains in the "physiologic" frequency ranges of 0 to about 300 Hertz are also typically used. This output is delivered to electrodes placed near to in neural tissue on a temporary basis (acute electrode placement) of permanent basis (chronic electrode implants). Such stimulation can relieve pain, modify neural function, and treat movement disorders. Typically, in most cases the stimulation must be sustained to have long-term effects. That is, usually when the stimulus is turned off, the pain returns or the therapeutic neural modification ceases after a short time (hours or days).

Thus, it is standard practice to use permanent implant electrodes and stimulators, which may be operated on battery power or induction driven. An example of such a commercially available system is one manufactured by Medtronic, Inc., located in Minneapolis, Minn. With permanent implant electrodes and stimulators, the stimulus is usually sustained or repeated on an essentially continuous basis for years, to suppress pain or to treat movement disorders, for example, Parkinsonism, bladder control, spasticity, etc. Stimulators deliver regular pulse trains or repetitive bursts of pulses in a range between 0 to 200 Hertz, which corresponds to a human body's physiological range of neural frequency pulse rates. This method stimulates or inhibits neural function. It does not seek to heat the neural tissue for destructive purposes as in high frequency technique.

Chronologically or permanently implanted stimulators of the type discussed above, require frequent battery changes or long-term maintenance and patient follow-up, which is expensive and inconvenient, often requiring repeated surgery.

Electrosurgical generators have commonly been used in the past for cutting and coagulating tissue in surgery. They typically comprise a high frequency, high power generator, which is connected to an electrode that delivers its high power output to explode tissue for purposes of cutting, cooking, searing, or otherwise coagulating tissue to stop bleeding. Examples of such systems are generators available from a company named Codman, Inc., located in Randolph, Mass., or from a company named Valley Labs, Inc., located in Boulder, Colo., or from a company named EMC Industries, located in Montrouge, France. Such generators have high frequency output waveforms, which are either continuous waves or interrupted or modulated waves. Such generators have high power levels and duty cycles, which when applied to the electrode, shatter and macroscopically separate tissue (in a cutting mode) or heat the tissue to very high temperatures, often above cell boiling (100° C.) and charring levels (in a coagulation or cauterizing mode). It should be recognized that the purpose of electrosurgery generators is surgical, not therapeutic. Thus, their output controls, power ranges, duty cycles, waveforms, and monitoring capabilities are not designed for gentle, therapeutic, neuro-modulating, sub-lethal temperature applications. Use of an electrosurgical unit requires local or general anesthetic because of its violent effect on tissues, whose temperature levels are raised to very high levels.

SUMMARY OF THE INVENTION

The present invention is directed to a modulated high frequency system for use with a signal applicator such as an electrode, conductive plate, or structure, which is applied to a patient's body to modify its neural function. The present system advantageously relieves pain or modifies a patient's neural system without average heating the patient's tissue above 45° C. to 50° C., without stimulating it at frequencies in the range of 0 to about 300 Hertz, and without burning or cauterizing it. Thus, the present system avoids the painful effects of forming radiofrequency (RF) lesions at high temperatures and circumvents the need for chronic stimulation of the tissue.

In accordance with one preferred embodiment, the system generates an RF waveform output, which is coupled to an electrode inserted into a patient's body, near or in the neural tissue. The system, by interrupting the RF waveform with bursts of RF power interposed with periods of off-time, accomplishes a pain relieving effect or other neural modulating effect in a patient, without exceeding the tissue temperature beyond approximately 45° C. on average. With this system, the painful heat lesions formed near the electrode, with temperatures substantially greater than 45° C. are avoided. The modulated RF system of the present invention may be used painlessly and easily, avoiding usual discomforts inflicted by standard RF heating procedures. Yet relief from pain or neural disfunctions such as motor disfunctions, spasticity, Parkinsonism, tremors, mood disorders, incontinence, etc., are long lasting, yielding results in many cases that are comparable to, if not superior than, results from RF heat lesions formed at much higher temperatures.

Some applications of the system and method in accordance with this invention may include relief from back, head, or facial pain, by procedures such as dorsal root ganglion or trigeminal ganglion treatments, spinal cord application for relief of intractable pain, spasticity, or motor control, treatment of the basal ganglia in the brain for relief of Parkinsonism, loss of motor control, tremors, or intractable pain. This pain relief or control of elimination of motor or other neural disfunction is comparable if not more effective than relief from long-term stimulators with implanted electrodes. Besides, the need for permanent implants, expensive implanted devices and circuits, battery changes, involving repeated surgery and expense, and repeated application of stimulation energy over long periods (months and years) is avoided.

Advantageously, unlike electrosurgical systems, the present system accomplishes pain relief or neural modification in patients in a non-violent, painless manner, avoiding average tissue temperature elevations into the lethal range and violent macroscope tissue separations.

Different embodiments of the present modulated frequency generator and its output waveforms are disclosed in this application. Some embodiments with temperature monitors and thermal sensing electrodes are disclosed, which serve to control the modulated system and its use in some applications. For example, by using a temperature monitor in the tissue, to which the modulated radiofrequency output is applied, a surgeon may monitor the temperature of the tissue and thus, avoid RF voltage or current levels, which would raise the tissue to lethal thermal levels (which are generally beyond 40° C.–50° C.).

Specific processes for implementing the modulated high frequency neural modulation and the details of applying the high frequency or radiofrequency (RF) voltage, current, or power to the patient's tissue, with and without temperature monitoring to achieve desired clinical results, are described below.

BRIEF DESCRIPTION OF THE DRAWINGS

In the drawings, which constitute a part of the specification, exemplary embodiments exhibiting various forms and features hereof are set forth, specifically:

FIG. 12 illustrates the use of intensity modulated high frequency electrical signal applied to acupuncture needles;

FIG. 13 shows a schematic diagram of a percutaneously placed electrode and differential pulsed RF versus thermal tissue alternation zones;

FIG. 14 shows applications of modulated high frequency to internal and surface structures of the brain by depth and surface electrodes.

DESCRIPTION OF SOME PREFERRED EMBODIMENTS OF THE INVENTION

Figure 1:
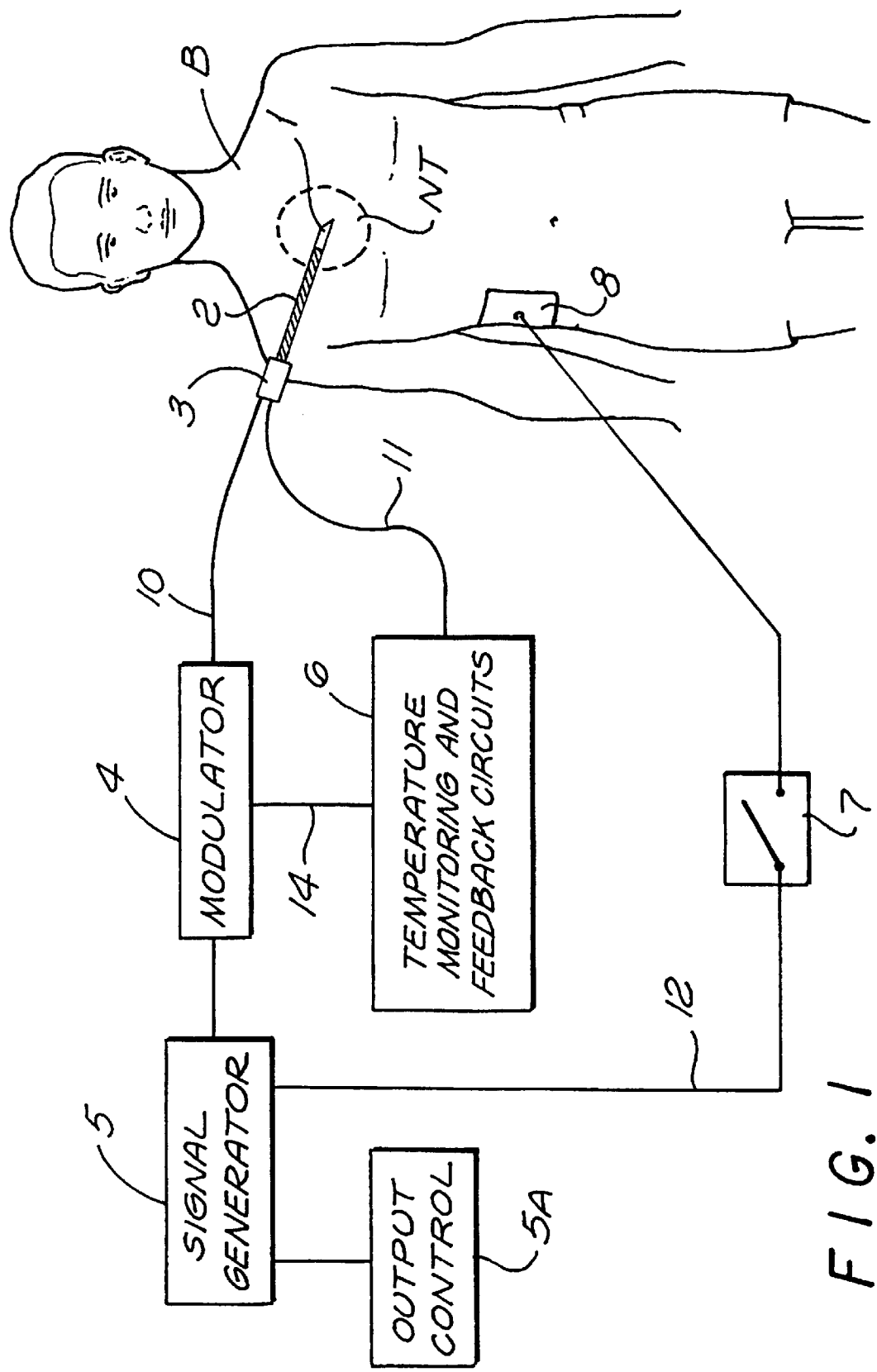
FIG. 1 is a block diagram of the various elements and portions of the overall system in accordance with the present invention.

Referring to FIG. 1, an illustration of the system and the method in accordance with the present invention in shown by a block diagram and schematic elements. An electrode with an uninsulated conductive surface 1 (for example, a conductive tip end) is shown in the proximity of a region of neural tissue NT illustrated schematically within a dashed boundary. The electrode has an insulated shaft 2 (shown by the cross hatched lines) and connection or hub portion 3, inside of which there may be electric connections to the surface 1. A connector 10 electronically connects to the surface 1 through the electrode shaft 2 and to electronic supply units 4 and 5 (which are illustrated outside the body, but which alternatively, may be miniaturized and implanted inside the body). The electronic supply unit 5 represented in block form is a signal generator having a signal output, which may be voltage, current, or power. The electronic supply unit 4 is a modulator to modulate (for example the amplitude of) the high frequency output from the signal generator. The output from 4 and 5 is an electrical output signal such as an electromagnetic or other signal known to one skilled in the art, which is connected to the electrode surface 1, and therefore, is conductively exposed to the tissue NT.

By way of an example, the signal generator element or device 5 may take the form of an RF power source with a continuous wave output. One example of such a power source is a generator identified by Model No. RFG-3C, which is available from Radionics, Inc., located in Burlington, Mass. The block indicated by reference numeral 4 in one example represents a pulse modulation unit, which switches the RF output from the signal generator 5 on and off, at a designed rate and duty cycle. Use of RF output generators or supplies and modulation circuits are known in the use of high frequency techniques (which for example, are described in a book entitled Radio Engineering by Frederick E. Terman, McGraw-Hill, New York, 1947, 3rd Edition). A temperature monitoring element or circuit 6 is also shown, which is connected by a cable 11 to the electrode and to a thermal sensor, which may be a thermistor or thermocouple, disposed inside the electrode applicator or conductive tip 1 to measure the temperature of the tissue NT near the tip. An example of such thermal sensing circuits and electrodes is one identified by Model No. RFG-3C available from Radionics, Inc., located in Burlington, Mass. Furthermore, FIG. 1 illustrates a reference electrode 8 shown in electrical contact with the patient's body B with connection wire 12 running to the generator 5 so as to provide a circuit for return current from electrode applicator 1 through the patient B (such reference electrodes are common with RF lesion generators; as discussed in the research papers by Cosman, et al., entitled "Theoretical Aspects of Radiofrequency Lesions and the Dorsal Root Entry Zone," *Neurosurgery* 15:945–950, 1984; and Cosman E R and Cosman B J, "Methods of Making Nervous System Lesions," in Wilkins R H, Rengachary S S (eds): *Neurosurgery,* New York, McGraw-Hill, Vol. III, 2490–2498, 1984). A switch or circuit breaker illustrated by element 7 illustrates that such a return circuit could be opened to limit such direct return current, and limit such current to inductive or reactive current characteristic of time varying circuits such as RF circuits.

In operation, the voltage or current output from the signal generator 5 and the modulator 4 are impressed upon tissue NT, which may be neural tissue (for example, spinal nerves or roots, spinal cord, brain, etc.) or tissue near neural tissue. In accordance with the present invention, such an electrical output, for example, an electromagnetic output, can cause energy deposition, electric field effects, and/or electromagnetic field effects on the nerve cells in the tissue NT so as to modify or destroy the function of such nerve cells. For example, modification of neural function may include reduction or elimination of pain syndromes (such as spinal faces, mechanical back pain, facial pain) in some cases, alleviating motor disorders. Because the RF output from 5 is modulated by element 4, its percent on-time is reduced so that sustained heating of tissue NT is reduced, yet the neural therapeutic effects of the impressed RF voltages and currents on the neural tissue NT are enough to produce the pain reducing result. The signal generator 5 may have a power, voltage, or current output control 5A (as on the Radionics Model RFG-3C RF generator) to increase or decrease the output power magnitude or modulated duty cycle to prevent excessive heating of tissue NT or to grade the level of pain interruption as clinically needed. Output control 5A may be a knob, which raises or lowers the output in a smooth, verniated way, or alternatively, it may be an automatic power control with feedback circuits. In this regard, the temperature monitor 6 provides the operator with the average temperature of tissue NT near electrode tip 1 to interactively prevent temperatures near tip 1 to exceed the range of approximately 45° C. (on average thermally lethal to tissue NT), and thus, to avoid the higher temperature ranges for the usual heat lesioning procedures described above. For example, element or circuit 6 may include feedback circuitry to change the modulation duty cycle (by, for example, longer or shorter on-times) to hold the temperature near tissue NT to below a set value (for example, 40° C. to 45° C.), illustrated by the feedback line 14 in FIG. 1. In addition, the high frequency waveform from the signal generator 5 is free from substantial components in the 0 to about 300 to 400 Hertz range (which is much lower than radiofrequencies), and this avoids the stimulation effects that are typical for stimulator system applications as described above.

Figure 2:
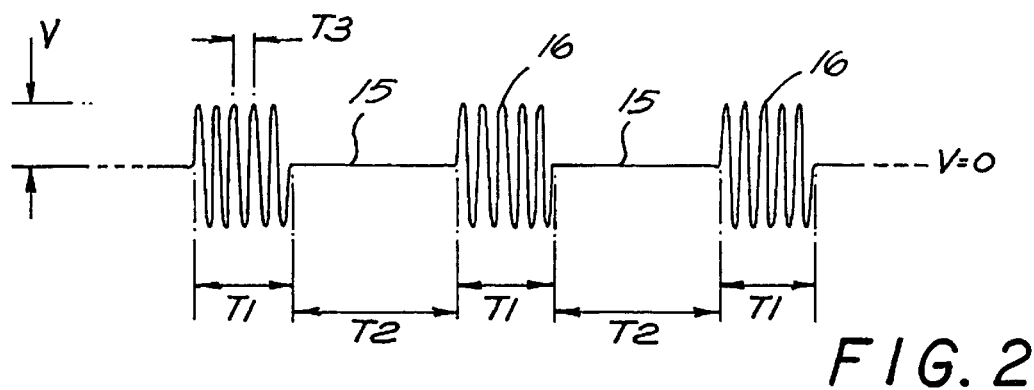
FIG. 2 is a graphical representation of an exemplary interrupted RF waveform output from an RF generator system in accordance with the present invention.

As an example of a modulated RF waveform that accommodates the system of the present invention, FIG. 2 shows schematically a high frequency output with a voltage amplitude V and with a burst duration T1 between which on-time bursts there are illustrated periods of zero voltage of duration T2. During the on-time T1, the RF signal output is oscillatory with time period T3 between maximum voltages V. The reciprocal of T3 is proportional to the value of the radiofrequency (for example, 1 Mega Hertz RF output corresponds to T3=1 microsecond). This is an interrupted or bursting type of modulated high frequency waveform. During the high frequency on-time T1, the voltage may oscillate between plus and minus its maximum value V. Accordingly, an electric field is produced round the region of the electrode applicator (as for instance the exposed electrode tip 1 in FIG. 1). The electric field induces a modifying, or pain-relieving, or neural-altering effect on the tissue near or among the nerve cells and fibers. Pain relief and neural modification may accordingly be accomplished by this high frequency bursting voltage and accompanying electromagnetic field, and also accompanying current among the neural and tissue cells. During the off period, there is minimal or no voltage (i.e. V=0 at the electrode applicator), and thus, no electric field or electric currents in and among the neural tissue. During that period, no heat deposition is present. Thus, over the entire cycle, from on period T1 through off period T2, the energy deposition, on average, may be adjusted so that there is no excessive heating, on average, around the electrode applicator. Thus, the usual mechanism of continuous on-time high frequency voltage and current, as in previous heat lesion techniques, is avoided. Therefore, the achievement of high average temperatures near or around the applicator tip may be eliminated by the present invention. The usual heat lesion process in which tissue temperatures, on average, exceed 45° C., may also be avoided. In many instances, this avoidance of high temperature domains due to high average heat dissipation of the radiofrequency power prevent acute pain of the process to the patient. By having the interrupted waveform, as in FIG. 2, the average power is thereby reduced and the average heating around the electrode tip or applicator is accordingly also reduced. However, substantial voltages V (or currents) are still sustained during the on period with their resulting therapeutic effects on the tissue.

To give a representative example of values for parameters in an interrupted high frequency waveform as in FIG. 2, the overall pattern of the waveform may have a total period of one second, meaning that the sum of T1+T2=1 second. The on period T1 may be 20 milliseconds, and the off period T2, therefore, may be 980 milliseconds. Voltages V in the range of 10 to 30 volts or more may be used. It may be used to induce a pain relieving effect in certain tissues. Average tip temperature around an electrode tip such as the exposed tip element 1 in FIG. 1 may be maintained at or below 40° C., well below thermo-lethal levels. Electrodes with diameters of 1 or 2 mm shaft (for example, the shaft 2 of a cannula in FIG. 1) may be maintained at or below 40° C., well below thermo-lethal levels. Electrodes with diameters of 1 or 2 mm shaft (for example the shaft 2 of a cannula in FIG. 1), with an exposed tip of 1 to 10 mm (such as the tip element 1 in FIG. 1) may be used and the electrode may be inserted in around neural structures in the brain or peripheral nerves or peripheral nerve ganglia to accomplish pain relief or other neurological alteration. Variations in these parameters may be made with similar therapeutic effects, and various geometries of conductive electrodes or applicators may be effective. Illustrations of a wide variety of such electrodes are available in the product Line of Radionics, Inc., located in Burlington, Mass. Pointed or sharpened electrodes (such as illustrated schematically by electrode tip in FIG. 1) are useful for penetration of the electrode through the skin to the target neural tissue site, and electric or current fields or higher intensity will be present at a sharpened point for a given applied voltage (such as V in FIG. 2), which will be effective in altering neural function.

Figure 3:
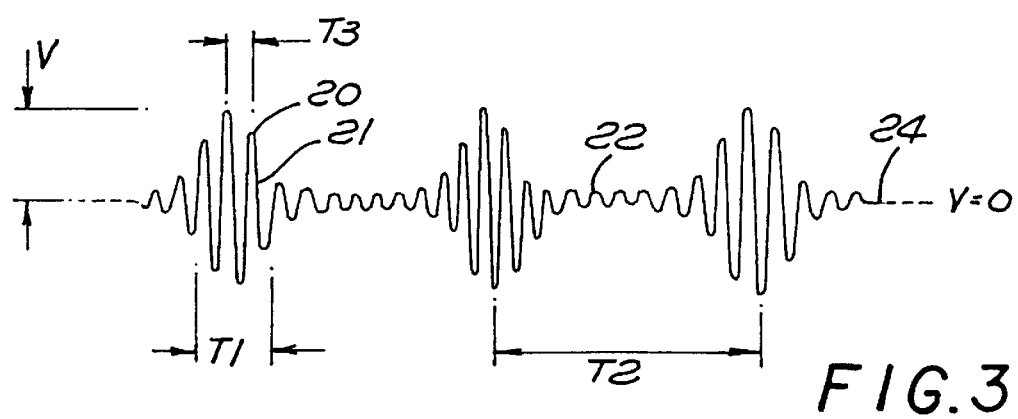
FIG. 3 shows a graphical representation of a modulated frequency waveform in accordance with the present invention.

FIG. 3 shows a variation of the modulated high frequency waveform, which accomplishes high peak voltage swings with reduced average power deposited in tissue. The baseline voltage may be put at zero (that is, V=0), shown by the dashed line 24. The solid line 21 represents the actual waveform, which has rapid oscillations at the radiofrequency and has an overall enveloped, represented by dashed line 20, that has high points and low points with an approximate on time T1 and a time period between the envelope of modulation maxima T2. T1, again, may be a percentage on time of 2 percent (as described above for 20 milliseconds on time out of 1 second total), and this on time T1 may vary considerably while still maintaining substantial off time so as to prevent overall average high temperature heating (as in the usual RF heat lesion systems). Such a modulation envelope (as shown by dashed line 20) may be achieved by using a modulated signal generator that varies the input or output gain of high frequency generator (for example element 5 in FIG. 1) so as to achieve such a waveform as in FIG. 3. In such circuitry, which is commonly used in pulse generation techniques, low frequency filtering or selection of modulation parameters may avoid stimulation voltage or current components at the physiologic range of 0 to 300 Hertz so that unpleasant stimulative effects may be avoided during the therapeutic intermittent high frequency lesion process.

Figure 4:
FIG. 4 illustrates an irregular frequency output waveform in accordance with the present invention.

FIG. 4 shows yet another embodiment of an interrupted high frequency waveform in accordance with the present invention. Here there is a non-periodic variation of the voltage represented by the excursions of the voltage V represented by excursions on a vertical axis. The maxima point 25 may occur at random positions in time. The time difference between maxima may also vary in an irregular or even random way. This waveform may have no repeating or periodic structure, but may be analogous to high frequency noise with random amplitudes, peaks, zero crossings, and carrier high frequencies. Such a waveform may be generated by random noise generators, spark gap signals, or other noisy signals that are known in the field of signal generation (for example, as described in *Radio Engineering*, cited above). Filtering may be applied in the wave generator and power amplifier so that lower frequencies in the physiologic range are not present to cause undesirable stimulation effects.

Figure 5:
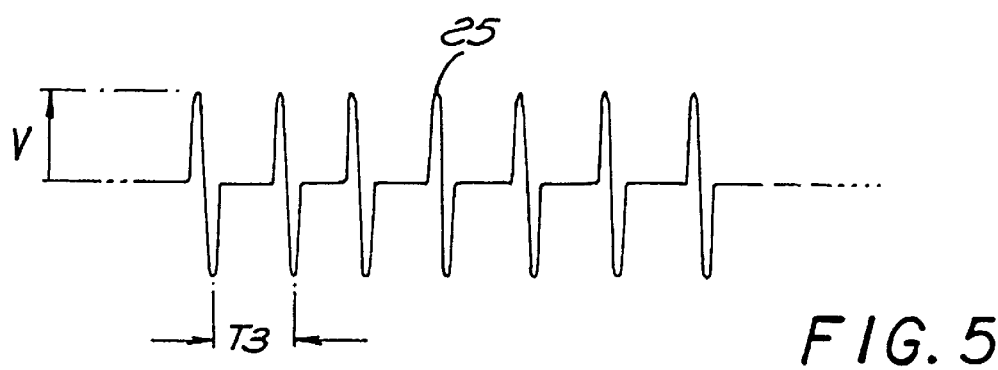
FIG. 5 shows repeated frequency signals with a lowered output duty cycle.

FIG. 5 shows yet another possible high frequency waveform of interrupted, repeated bipolar pulses with frequency repetitive time T3 for example, the physiologic stimulation frequency range (i.e., 0 to about 300 Hertz). The pulse on-time may be low enough so that the power deposition may be kept low enough to prevent heating, and yet the peak voltage V is enough to alter the neural function.

Variations of such waveforms are possible with the same intermittent high frequency effect for pain or neurological modification. For instance, a baseline V=0 may not pertain and a slowly varying baseline of non-zero value may be used. The time average of the signal need not be zero. The on and off switching of a high frequency signal such as in FIG. 2 may be done at a non-periodic or non-regular, repeating rate so that, on average, the polarization effects in the tissue are still maintained at a low level. The average power deposition may still be maintained at a low level with non-periodic, interrupted high frequency waveforms. The high frequency carrier frequency (i.e., represented by the inverse of time T3 in FIG. 2 and FIG. 3) may also be non-constant. Varying or combined or superposed high frequency waveforms may be used as the carriers, and the combined or composite high frequency waveforms may be interrupted or modulated in accordance with the present system and invention. Pulse waveforms with high frequency carriers may be shaped in a variety of ways, for example, with fast rising leading edges and slowly falling off or exponential trailing edges. The signal generator waveform may have a peak intensity, which is much higher than the average or RMS intensity to yield a high electromagnetic field or current density on the neural tissue while maintaining the average power deposition in the tissue at a sufficiently low level to prevent heating above lethal tissue temperatures (for example 40° C. to 50° C.).

Figure 6:
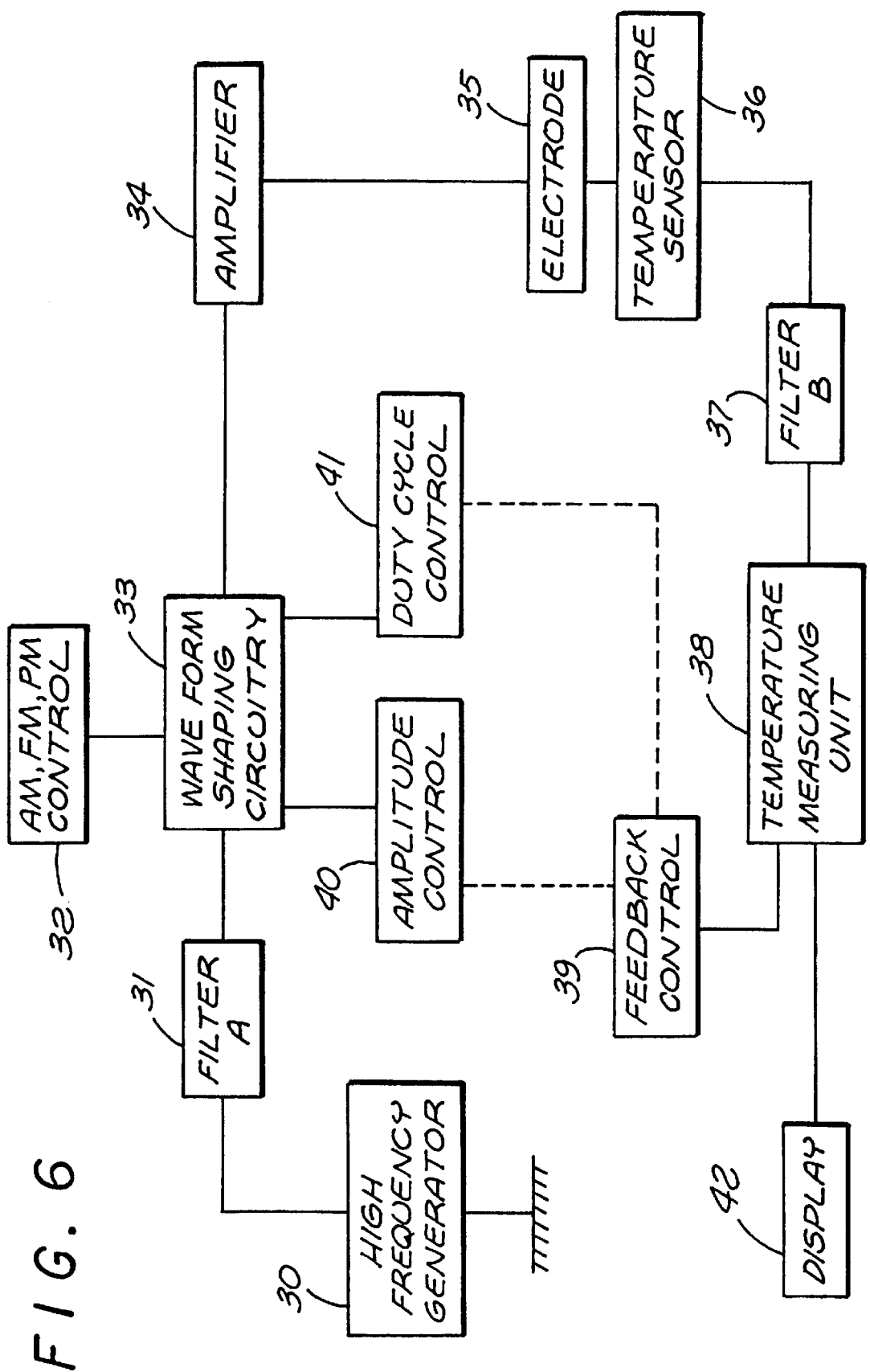
FIG. 6 is a block diagram of the various elements of the system for generating modulated frequency signals.

FIG. 6 shows a more detailed block diagram of the system for generating modulated high frequency signals (similar to but more detailed than the block element of high frequency generator 5 and modulator 4 of FIG. 1).

A block or element 30 represents a signal generator, which may create a high frequency signal or periodic or non-periodic frequency. The signal generator 30 provides an input to a filter system 31, which selectively filters out frequencies that could cause unpleasant, undesired, or damaging physiological signals. The signal is then fed into a waveform shaping circuit 33, which shapes the waveform input from a block or element 32, which provides amplified modulation and/or frequency modulation and/or phase modulation control. Circuits of this type are described for instance in *Radio Engineering* by Terman (cited above, in a book entitled *Radio Engineering* by Frederick E. Terman, McGraw-Hill, New York, 1947, 3rd Edition). Additional waveform shaping may be done by elements 40 and 41, which control the amplitude of waveform and/or the duty cycle of the waveform, respectively. The resultant signal is then fed into a power amplifier 34. This is a wide band amplifier used to increase the signal to power levels appropriate for clinical use. This energy is then delivered to the patient via an electrode represented by element or block 35.

A temperature sensor or plurality of temperature sensors, represented by 36, may also be placed and connected proximate the electrode so as to insure that the temperature does not exceed desired limits. This temperature sensor signal is fed through a filter B represented by 37, which is a special filter module used to eliminate high frequency components, and thus, not to contaminate the low-level temperature signals.

The temperature signal is fed to a standard temperature measuring unit 38 that converts the temperature signal into a signal that may be used to display temperature and/or to control, in a feedback manner, either the amplitude and/or the duty cycle of the high frequency waveform. In this way, power delivery may be regulated to maintain a given set temperature. This flow is represented by block or element 39, which is simply a feedback control device. The dotted lines from element 39 to elements 40 and 41 represent a feedback connection that could either be electronic and/or mechanical. Alternatively, a person may simply operate these controls manually, based on the visual display of temperature, as for example, on a meter or graphic display readout 42.

As was explained with respect to the disclosed embodiments, many variations of circuit design, modulated high frequency waveforms, electrode applicators, electrode cannulas will be appreciated by those skilled in the art. For example, many electrodes or electrode applicators are practical, including tubular shapes, square shafts, flat electrodes, area electrodes, multiple electrodes, arrays of electrodes, electrodes with side outlets or side-issued tips, electrodes with broad or expandable or conformal tips, electrodes that may be implanted in various portions of the brain, spinal cord, interfacial space, interstitial or ventricular spaces, nerve ganglia may be considered with the system of the present invention.

The frequency range for the so-called high frequency waveforms, as shown for instance in FIGS. 2, 3, 4, and 5 may be used over a wide range. For example, the "high frequency" characteristic of 1/T3, which may be only one of many high frequency components, may be above the so-called physiological stimulation frequency range of 0 to about 300 Hertz. This high frequency may also extend up into the radiofrequency or microwave range (for example, 50 Kilo Hertz to many Mega Hertz).

Mixtures of frequencies may be accomplished as discussed above. These may be mixtures of "high frequencies" (above the physiologic stimulation) range of (say 0 to 300 Hertz) and lower frequencies (within that stimulation range of say 0 to 300 Hertz). Thus, one skilled in the art may have both modulated high frequency and stimulation frequencies for various clinical effects, such as stimulation blockage of pain while neural modification is being applied according to the present invention.

Figure 7:
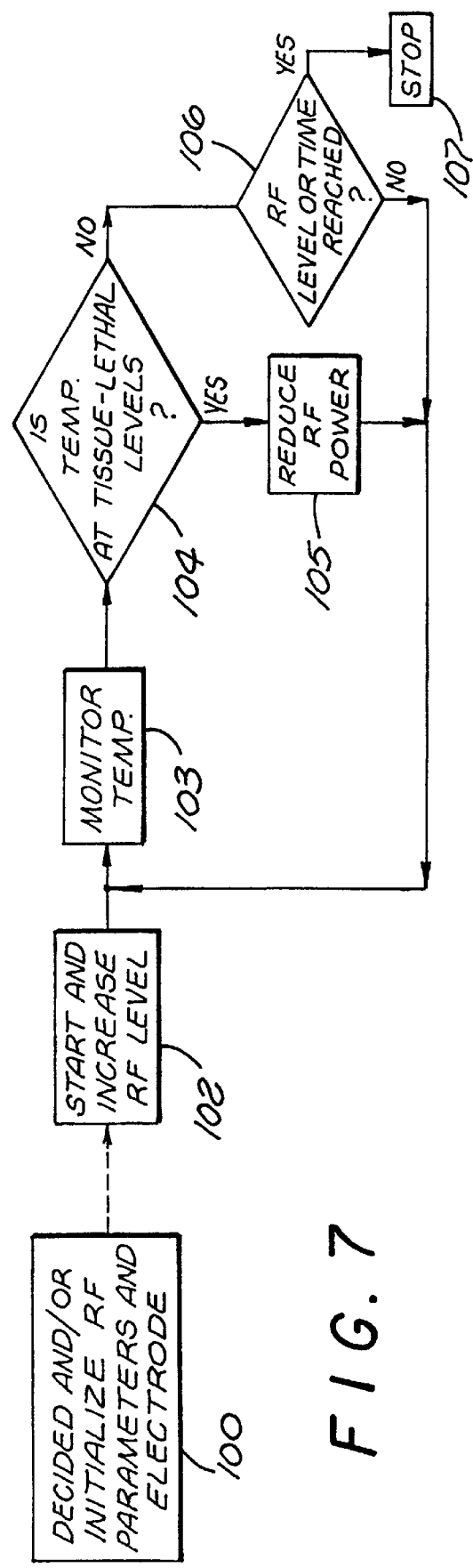
FIG. 7 is a flow diagram of the process in accordance with the present invention.

Referring now to FIG. 7, the operation of the system and method is shown with a flow diagram. Assume that an electrode 1 is placed in contact with the patient's body and connected to a modulated high frequency generator (represented by blocks 5 and 4) in the manner described above. Once the electrode 1 is in place, a clinician may decide on the desired electrode parameters and modified high frequency parameters that should be used. This is indicated by initialization block 100 in FIG. 7. For example, for a given electrode geometry or location of electrode 1 in the patient's body, it may be decided that a certain duty cycle of high frequency signal, voltage, current, or power level of high frequency signal, or a mixture of high frequency signal and stimulation signal may be desirable. Furthermore, a choice of electrode for a given application involving a suitable electrode geometry (for example, sharpened electrode shaft, catheter-type electrode, surface electrodes for skin application, flattened electrodes for cortical or spinal cord application) may be made. Alternatively, the modified high frequency generator may have fixed parameters, which are used universally for certain types of procedures, in which case the initialization block element 100 in FIG. 7 may not be present. This is symbolized by the dashed line between block element 100 and block element 102.

A block or element 102 indicates the start of the high frequency application in which an "on" button may be pulsed, and the elevation of high frequency, voltage, current, or power (level) is started. In a case where the temperature sensor is disposed in or near the electrode applicator connected to the patient's body, the temperature monitor 103 is indicated, which may sense that temperature and monitor or read it out to the clinician. Alternatively, temperature sensing may also be conducted away from the output applicator. For instance, a separate temperature sensor may be inserted at a position located at a distance from the active RF electrode. Increasing the RF level 102 to achieve the neural modification effect (for example, pain relief for the patient) is accomplished by the electromagnetic, electric, or other aspects of the high frequency field in the presence of the neural structures. If the temperature monitor 103 shows that the temperature of the tissue is being elevated to lethal levels (from 40° C. to 50° C., for example, then the decision block or element 104 determines that if these levels are reached, a reduction of the RF power (block or element 105) may be implemented so as to reduce the temperature monitored level 103. If lethal temperature levels have not been reached, there is the option to continue with raising the RF level or to hold it static at a desired, predetermined level until the proper clinical effect has been reached. At end point of a particular RF level or time duration for the exposure indicated by element 106 may be utilized, and when an RF level or time has been reached, then the unit may be shut off, as indicated by block or element 107.

Figure 8:
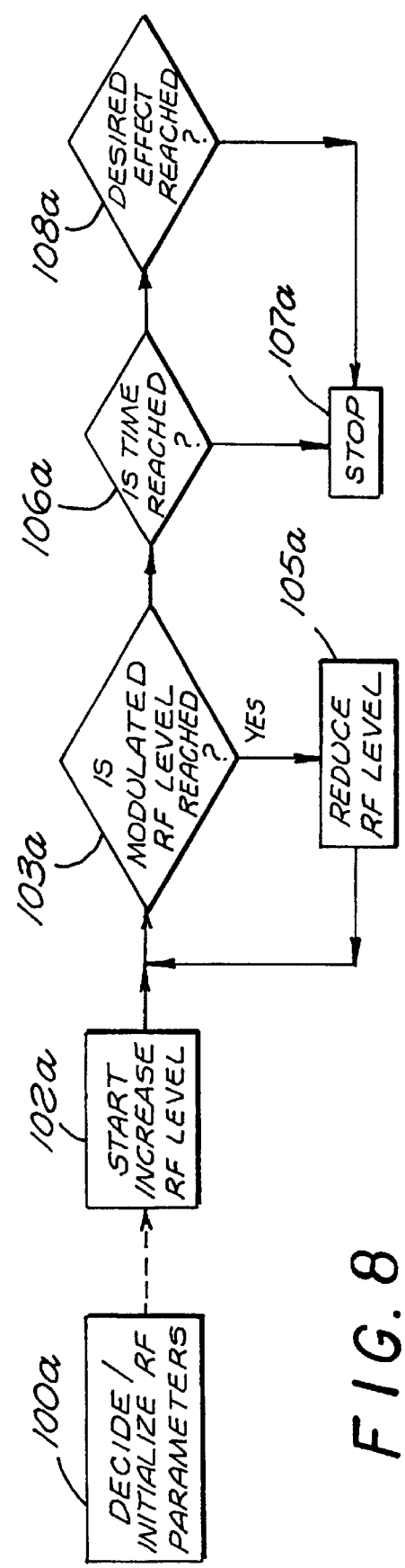
FIG. 8 is another flow diagram of the process in accordance with the present invention.
Figure 9:
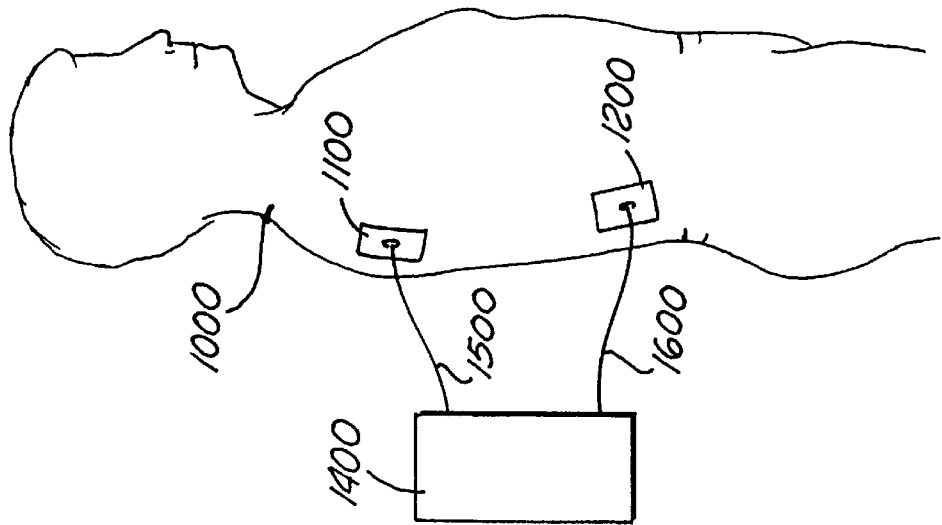
FIG. 9 shows a transcutaneous surface application in accordance with the present invention.

Referring to FIG. 8, another flow diagram for cases is shown where temperature monitoring is not conducted. In such situations, it may be decided by block element 100a that some target parameters for the high frequency field (such as voltage, current, or power level) will be used in a given anatomical region and for a given electrode 1. The RF level is increased in step 102a, and if the level of modulated high frequency output is reached (determined by decision block or element 103a), then, a feedback may take place to reduce that level as represented by block or element 105a. Element 103a may simply be a manual control or RF output control knob or it may be done by electronic feedback on the RF power amplifier or signal generator. This same type of feedback system may be, for example, illustrated by the continuous wave radiofrequency generators, such as one identified by Model No. RFG-3C available from Radionics, Inc., located in Burlington, Mass. If the parameter criteria for an adequate procedure is a certain time duration, then in the decision process, if that time is reached, element 106 may be actuated and the system stopped when that desired time duration has been reached. Variations of pulsed radiofrequency signals could be applied ranging from several seconds to several minutes or more depending on the clinical conditions. In one clinical example, an average tip temperature of 42° C. (degrees Celcius) was maintained, and a continuous RF signal from the radio generator 1400 (see FIG. 9) was applied for 120 seconds. However, it should be recognized that depending on the clinical conditions, the RF signal may be applied for a period ranging anywhere from several seconds to several minutes. If time duration is not the desired end point parameter, then possibly the observation of a desired clinical effect such as abolition of pain, tremor, spasticity, or other physiologic parameter may be the desired criteria, as shown by element 108, again to make the decision to stop the procedure, as in element 107.

Various configurations of electrodes may be used with this modified high frequency technique for neural modification. For example, in FIG. 9, the patient's body 1000 may have applied to it surface electrodes 1100 and 1200, which may be connected to the high frequency generator 1400. Generator 1400 has a modified high frequency signal such as described above. Its output may be applied via wires 1500 and 1600 to the surface-based applicators to induce neural modification in nerve cells at the surface of the body or just below the surface.

Figure 10:
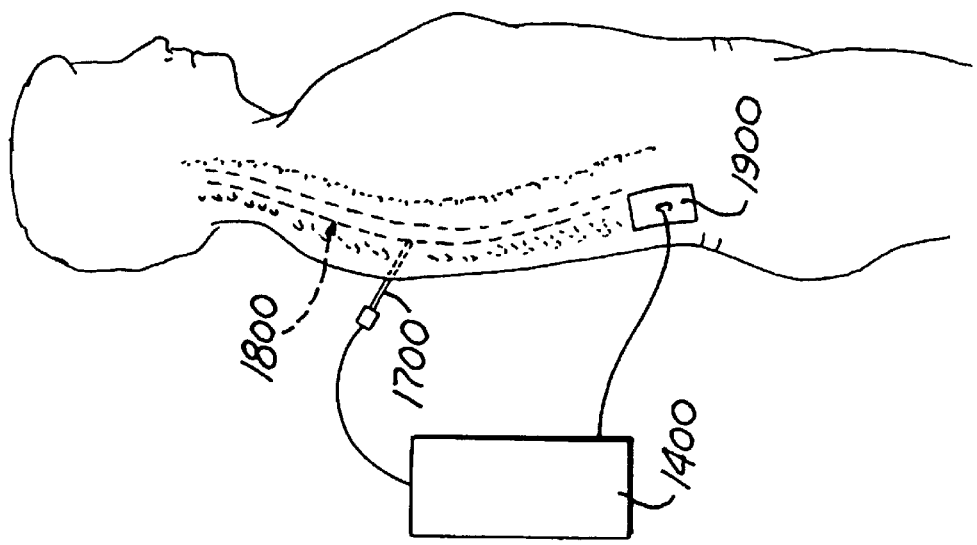
FIG. 10 illustrates a spinal pain relief procedure in accordance with the present invention.

FIG. 10 in another embodiment of the present invention, which involves implanting an electrode shaft 1700 near the patient's spinal column 1800. This might be done in the case of facet denervation, dorsal root ganglion modification, or other neural structure modification in or near the spine. The generator 1400 is again similar to one described above with a modified high frequency signal to cause neural modification of the spinal nerves in and around the spinal column 1800. This may be effective in alleviating back pain, headache pain, or other spinal diseases. The reference electrode 1900 is applied to the body as a return current source.

Figure 11:
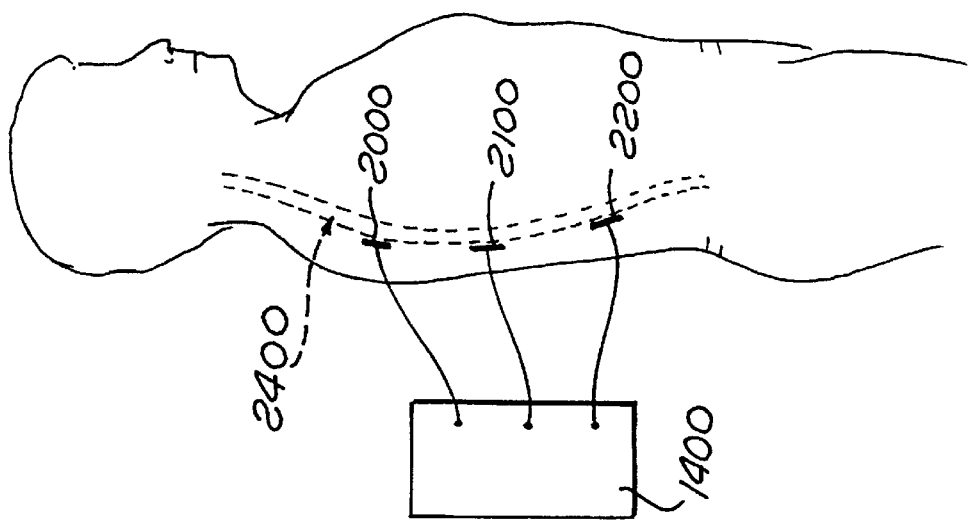
FIG. 11 illustrates a multi-electrode dorsal column application for pain relief in accordance with the present invention.

FIG. 11 shows the application of the present invention for spinal cord or dorsal stimulation where multiple electrodes attached to a catheter or flat strip electrode are used (such electrodes are available from Medtronic, Inc., located in Minneapolis, Minn. or Radionics, Inc., located in Burlington, Mass.). In this figure, modulated high frequency generator 1400 is shown with multiple outputs connected to electrodes 2000, 2100, and 2200, which may be implanted or on the surface of the spinal cord, as illustrated by element 2400. The electrodes 2000, 2100, or 2200 may be greater in number, and they may be inserted through a catheter or serial string element, which may be tunneled near the spinal cord percutaneously. Application of the neural-generated output from 1400 may cause pain relief, relief of spasticity, relief of other neural disfunctions by the neural modification as described in the previous application.

Variations of the processes and configurations of the above figures are possible by those skilled in the art.

Variations of the steps in a high frequency neural modification procedure may be varied from those in FIGS. 7 and 8. Automatic feedback of temperature control, for instance shown in FIG. 7, may give rise to control of the RF level in element 102 of FIG. 7, so as to lock on a set temperature, illustrated by element 104, whereby the system may maintain a sub-lethal tissue temperature in the presence of the high frequency applicator. Other variations of electrode geometry and location in the body from those illustrated in FIGS. 9, 10, and 11 as well as others may be devised in the brain, spinal cord, peripheral nerves, or other neural structures anywhere in the body. Clinical criteria for the desired end-point parameters of the RF generator, electrode, time duration, temperature levels, may be applicable by those skilled in the art or to achieve a particular clinical end result. The set temperature below which the tissue temperature should stay is somewhat variable in the range of normal tissue temperature (37° C.) up to or about 50° C., wherein cell structures and neural cells die under sustained exposure to such elevation of temperature (discussed in the papers by Cosman et al.).

FIG. 12 shows yet another embodiment of the present invention in which multiple electrodes 2500, 2600, and 2700 are inserted into various portions of the body and connected to a pulsed RF generator or modulated high frequency generator 14 via the outputs 2800, which may be coincident or sequenced. Connection 3000 is made via connector wire to 3100, which is a reference electrode, or may also be used as an area electrode for electric field operation. The percutaneous electrodes 2500, 2600, and 2700 may be acupuncture electrodes or similar very fine gauge electrodes. Acupuncture electrodes may be put into various trigger zones within the body, and the modulated high frequency signal from 1400 may enhance the anesthetic effect of these electrodes or produce pain relief as described above. Thus, the present system may be used to enhance acupuncture type techniques.

FIG. 13 illustrates the differential effects of the modulated RF fields for tissue or neural tissue modification. Electrode 3600 with insulated shaft, except for exposed tip 3700, is inserted into the body or into an internal organ. The tissue of the body is element 1000. The electrode is connected via connection 3500 to a high frequency generator 1400, which may have a reference line 1600 connected to reference electrode 1900. The dashed portion of line 1600 illustrates that this connection may or may not be made by an electric current-carrying wire, but it rather may be a reactive or capacitive connection with no wire. The generator may produce sufficient root means square (RMS) high frequency power output to produce an isotherm contour 38, corresponding to a temperature greater than the conventional lesion mean temperature of approximately 45° degree Celcius. For example, the line 3800 may represent an isothermic surface of 50, 55, or 60, or more degrees, and the tissue within the volume may be killed by a conventional heat lesion. Nonetheless, electric fields and current generated around the electrode tip 3700 from, for example, an electric voltage output from pulse generator 1400 may produce electric fields that can modify neural tissue out to a larger surface, illustrated by the dashed line 1400. Thus, the tissue between surface 3800 and surface 1400 may be, for example, neural tissue that is modified by peak voltage or current intensities from the modulated electronic output of generator 1400. That output, for example, could be pulsed, as illustrated above. Thus, there may be region of average thermal destruction (within zone 38) and a region of electromagnetic, magnetic, or electronic modification (in the shell between 3800 and 1400) as illustrated in FIG. 13.

If generator 1400 in FIG. 13 produces a pulsed radiofrequency signal, then the peak RF voltages, intensities, power, and currents would be higher than for a continuous wave radiofrequency generator that produces a similar thermal distribution, or the same size of lethal isotherm 3800. This difference in signal intensities and electronic qualities of the fields for pulsed versus continuous RF cases may produce different clinical results and tissue function modifications in accordance with this invention.

A clinical experience has demonstrated such differences. Clinical data for a group of patients (Group A) for dorsal root ganglion lesions with a percutaneously placed electrode (such as 3600 in FIG. 13) with tip exposure 3700 near the dorsal root ganglion, was gathered. An average tip temperature recorded from the electrode tip 3700 of 42° C. was achieved, and a continuous RF signal from generator 1400 was applied. With the electrode tip temperature held at 42° C. for such continuous radiofrequency wave, no appreciable pain relief was experienced by the patients in Group A.

Clinical data for a second group of patients, Group B, for a pulsed RF application was quite different for the same tip temperature. An identical electrode 36 with the same tip exposure geometry 3700 was inserted into the same region of the basal ganglion. In Group B, generator 1400 was a pulsed RF generator with a duty cycle of about two percent. All other conditions and clinical pain symptoms were the same for Group B as for Group A. The pulsed RF signal was applied with signal intensity to achieve an average temperature rise of 42° C. at the tip 3700 (the same as for Group A), but the result was a very significant elimination of pain for the patients in Group B, i.e., pulsed RF application, significant pain relief was achieved when the average tissue temperature near the electrode tip was held at 42° C. It is known from past experience that 42° C. is considered less than the conventional heat lesion or destruction temperature for tissue in such circumstances. For Group A, the same average tip temperature of 42° C. for a continuous RF signal application did not produce significant neural modification or pain relief. Previous literature by Cosman et al. referenced above indicates that 42° C. is a "non-lethal" or "sub-lethal" lesion temperature, on average, for continuous RF signals, i.e. 42° C. is below a heat lesion level, yet at 42° C. there is significant neural modification or pain relieving effect for pulsed RF signals, illustrating the differential effects of pulsed high frequency signal and its associated electronic fields within the tissue compared to continuous RF fields for analogous temperatures, even below lesion levels. Such differential effects could include pain relief, motor function changes (as in Parkinsonism), spasticity relief, epilepsy relief or interruption, neuro-cognitive changes, mood alterations, and so on. In the clinical example above, pain relief was achieved without any of the usual sensory loss or other side effects associated with heat lesioning at higher temperatures, which is a major advantage of the low temperature pulsed RF method.

FIG. 14 shows another configuration with cortical C contact electrodes 2100 and 22, which may be flat area type electrodes placed on the brain surface at strategic positions to produce neural modification within the brain. The connection wire 4000 to generator 1400 supplies the high frequency signal to the electrodes 2100 and 2200. Multiple wires within cable 4400 may give different signals or a bipolar electrode configuration (see the discussion in Cosman's paper on radiofrequency fields) across the electrodes 2100 and 2200. Generator 1400 may also be connected to a catheter or rod-like electrode 4500, which would be placed deep into the brain and have electrode contacts 4000, 4100, and 4200 to produce the electronic high frequency field effects within the brain nearby. Again, multiple wires may be carried back to generator 1400 through the cable element 4600 for differential signal application on the contacts 4000, 4100, and 4200. Application of the pulsed RF fields in these configurations may give rise to functional modification of the brain. Alteration of epileptic seizures may be made by application of neuro-modifying, pulsed RF fields in such electrodes. Electrodes such as shown in FIG. 14 are common for recording in the study of epilepsy, as evidenced by brochures available from Radionics, Inc. Their use for high frequency application, however, may be applied to alter the brain function near sites where epileptic neural foci is thought to exist. Modification of these epileptic foci may modify or even abolish the epileptic seizure or disease. Similar implantation for application of deep brain or surface-type electrodes on the brain, spinal cord, or other portions of the body may have similar ameliorating or modifying effects on neural structures or other organs. For example, electrodes such as 4500 may be placed in the thalamus, pallidum, hippocampus, etc., of the brain for alteration or modification of movement disorders such as Parkinsonism, spasticity, epilepsy, etc. Again, these disorders may be removed or modified by the pulsed RF application.

Figure 15:
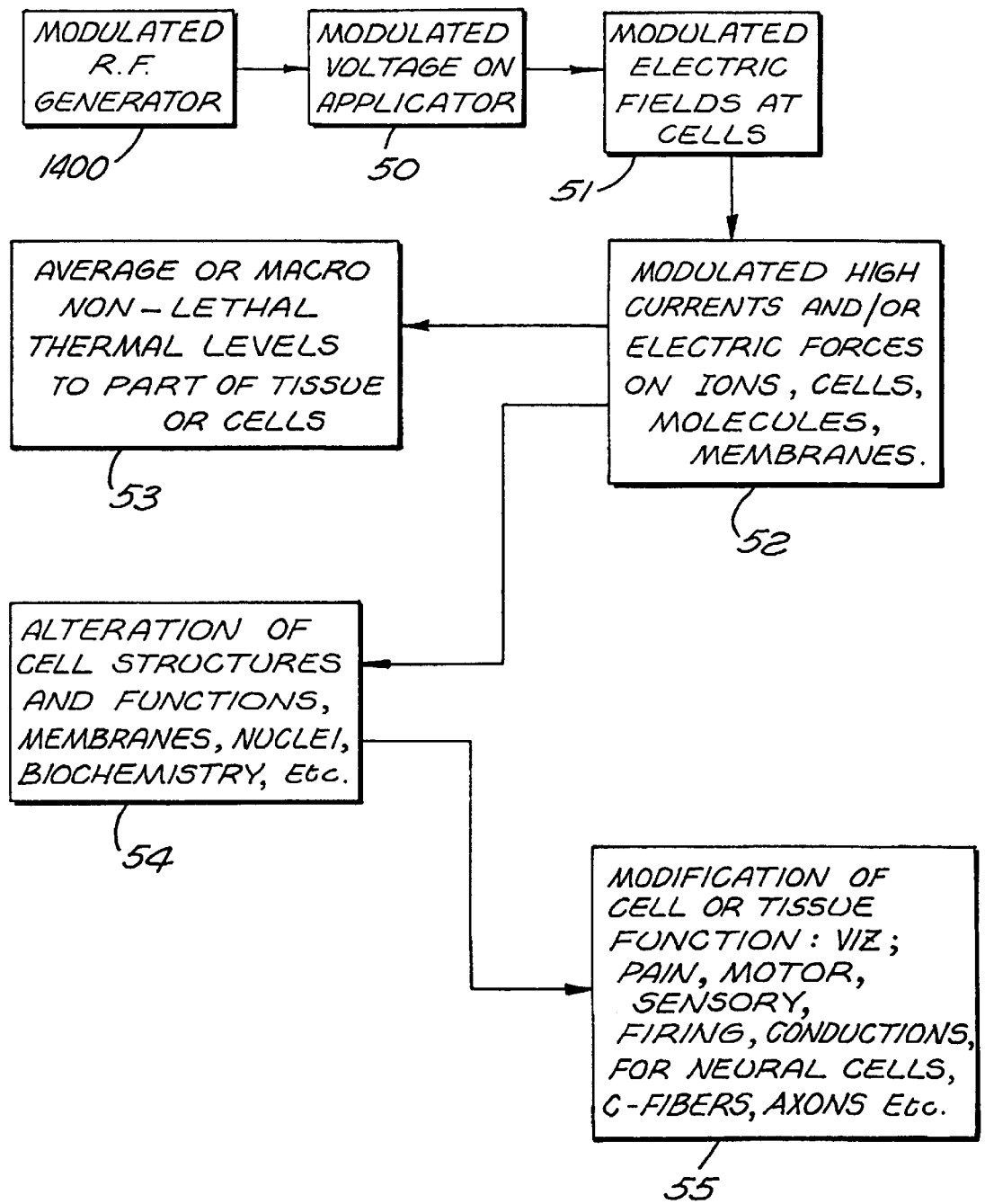
FIG. 15 shows a flow diagram for possible effects of the modulated high frequency generator output on tissue function.

FIG. 15 shows a schematic diagram of some ways in which modulated high frequency signals may affect cellular function. Modulated generator 1400 gives rise to a modulated signal output (e.g. voltage) applied to an applicator such as an electrode 1500. This may give rise to modulated electric fields on cells as illustrated by block 51. Electric fields will give rise to electric force or effects within the cells or the tissue (block or element 52). High RF fields produce alternating electric forces on ions, cell membranes, internal cell structures such as mitochondrion, DNA, etc., or forces of translation and rotation on polar molecules or on membranes having polar internal structures or charged layers. Ionic frictional dissipation effects may occur, (discussed in the articles by Cosman et al., cited above), producing average or macroscopic thermal elevation (block or element 53). If average power deposition is low enough, then the macroscopic thermal elevations will be at non-lethal levels. If power deposition is increased, the average temperature may exceed 45° C. (heat lesion levels). Yet even at low temperatures (for example 42° C.), electric forces and currents within the cell (block 52) may cause, nonetheless, neural modification effects (block or element 54) as in the clinical example above. Pulsed fields, voltages, or current may act on unmyelinated pain-carrying fibers such as C fibers differently from other more myelinated cells such as A fibers. The myelin sheath acts as a dielectric or capacitive protective layer on a nerve axon. C fibers, which primarily carry pain sensations, have minimal myelin sheath or no myelin sheath, and thus, may be more susceptible to strong pulsed electric fields, currents, or forces, even without significant heating of the nerve tissue.

The action of the modulated high frequency signal on neural tissue may eliminate pain while maintaining tactile, sensory, and other neurological functions relatively intact and without some of the deficits, side effects, or risks of conventional heat lesion making. Selectivity by pulsed RF fields may arise by selective deneravation of pain-carrying structures or cells (such as C fibers) compared to relatively non-destructive modification of other neural structures related to sensation, touch, motor activity, or higher level functions.

The selection of high frequency generator output parameters and the selection of electrode configurations such as size, shape, area, etc., may be interconnected to achieve a neural modification effect without excessive heating. At a given average power output of the generator as applied to the electrode adapter, a very small, sharpened electrode may give rise to high current densities in the tissue adjacent to it, which can give rise to focal heating, lesions, thermal cell destruction, cooking, and coagulation of nearby tissue. If the electrode chosen is larger, then such elevated temperature conditions may be reduced as the current density emitting from the electrode is reduced. In a given clinical setting, to achieve the desired neuro modification effect without macroscopic average elevation of neural tissue above, for example, the lesion temperature of approximately 45° C. (degrees Celcius), it may be necessary to select the appropriate parameters for both the lesion generator output such as voltage, current, power, duty cycle, waveform, etc., in coordination with the selection of the appropriate electrode geometry (the selection box, for example, being indicated by element 1 of FIG. 1). The system of electronic signal generator combined with the appropriate signal applicator to achieve a given neuro modification may then be considered in combination and cooperation to achieve the effect for a particular clinical site or result.

In view of these considerations, as will be appreciated by persons skilled in the art, implementations and systems should be considered broadly and with reference to the claims set forth below.

What is claimed is:

1. A system for altering a function of neural tissue in a patient comprising:

a) signal applicator adapted to apply an electrical signal output to said neural tissue;

b) a signal generator that generates a electrical signal output having at least one frequency component above a physiologic stimulation frequency range, said at least one frequency component producing an alteration of a function of at least a portion of said neural tissue, and said electrical signal output having a waveform that produces an average power deposition in the neural tissue corresponding to non-lethal average temperature elevation of said at least a portion of said neural tissue when said electrical signal output is applied to said neural tissue through said signal applicator; and c) a signal coupler that couples said signal generator and said signal applicator.

2. The system of claim 1, further comprising:

a temperature sensor that senses temperature of said at least a portion of the neural tissue and produces an output signal representative of said temperature; and a frequency component intensity control to adjust the intensity of the frequency component to maintain the temperature of the neural tissue below a lethal thermal level when said electrical signal is applied to said neural tissue.

3. The system of claim 1, wherein said electrical output signal is a radiofrequency signal.

4. A system for altering a function of neural tissue in a patient comprising:

a) an electrode adapted to apply an amplitude modulated electrical signal to the neural tissue of the patient;

b) a signal generator that generates an amplitude modulated electrical signal having at least one frequency component above a physiological stimulation frequency range, said amplitude modulated electrical signal producing an alteration of a function of the neural tissue while producing an average power deposition in the neural tissue corresponding to non-lethal temperature elevation of said neural tissue when the amplitude modulated electrical signal is applied to the neural tissue through said electrode; and c) an electrical coupling between said signal generator and said electrode to apply said amplitude modulated electrical signal to said electrode.

5. The system of claim 4 further comprising:

a modulation amplitude control that adjusts the amplitude of said amplitude modulated electrical signal.

6. The system of claim 4 wherein the amplitude modulated electrical signal has a peak voltage in the range of 10 to 30 volts.

7. A method for altering the function of neural tissue in a patient comprising the steps of:

a) generating an electrical signal having at least one frequency component above a physiologic stimulation frequency range, said at least one frequency component producing an alteration of at least a portion of said neural tissue, and said electrical signal having a waveform that produces an average power deposition in the neural tissue corresponding to non-lethal average temperature elevation of said at least a portion of said neural tissue when said electrical signal is applied to said neural tissue; and b) applying said electrical signal to said neural tissue.

8. The method of claim 7 further comprising the steps of:

a) sensing the temperature of said at least a portion of the neural tissue;

b) generating a temperature signal representative of the sensed temperature of said at least a portion of the neural tissue; and, c) adjusting the intensity of the at least one frequency component in response to said temperature signal in order to maintain the average temperature of said at least a portion of the neural tissue below lethal temperature levels when the electrical signal is applied to said neural tissue.

9. A system for altering a function of at least a portion of neural function of tissue in a patient comprising:

a) a generator that generates an electromagnetic signal having at least one high frequency component above a physiologic stimulation frequency range, said at least one high frequency component have a modulated waveform that produces alteration of the function of said at least a portion of said neural tissue when applied to said tissue through an electromagnetic signal applicator.

* * * * *